United States Patent [19]

Torii et al.

[11] Patent Number: 5,126,447
[45] Date of Patent: Jun. 30, 1992

[54] PROCESS FOR PREPARATION OF β-LACTAM DERIVATIVE FROM AN ALKENYL SUBSTITUTED β-LACTAM DERIVATIVE USING A RUTHENIUM OR RHENIUM CATALYST AND A PERIODIC ACID

[75] Inventors: Sigeru Torii; Hideo Tanaka, both of Okayama; Masatoshi Taniguchi, Toyonaka; Michio Sasaoka, Tokushima; Takashi Shiroi, Tokushima; Ryo Kikuchi, Tokushima; Yutaka Kameyama, Tokushima, all of Japan

[73] Assignee: Otsuka Kagaku Kabushiki Kaisha, Osaka, Japan

[21] Appl. No.: 662,605

[22] Filed: Mar. 1, 1991

[30] Foreign Application Priority Data

Mar. 2, 1990 [JP] Japan .................... 2-52445

[51] Int. Cl.$^5$ .............. C07B 41/06; C07D 205/095; C07D 205/085
[52] U.S. Cl. ............................ 540/358; 540/364; 568/488; 568/363
[58] Field of Search ............... 540/358, 360, 364

[56] References Cited

PUBLICATIONS

Neumann, J.A.C.S. 112, 6025 (Aug. 6, 1990).
Funk, J. Org. Chem 51, 3248 (1986).
Mehta, J. Org. Chem 52, 2875 (1987).
Torii, J. Org. Chem 50, 4980 (1985).

Primary Examiner—Mark L. Berch
Attorney, Agent, or Firm—Armstrong & Kubovcik

[57] ABSTRACT

A process for preparing a β-lactam derivative of formula (2) and/or the corresponding enol tautomer, which includes oxidizing an alkenyl-substituted β-lactam derivative of formula (1) in the presence of a ruthenium catalyst or a rhenium catalyst using a periodic acid:

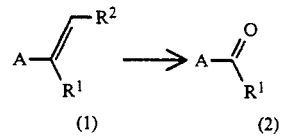

wherein $R^1$ is a hydrogen atom, a $C_{1-4}$ alkyl group or a $C_{1-4}$ haloalkyl group, $R^2$ is a hydrogen atom, a $C_{1-4}$ alkyl group or a phenyl group which may have a substituent, A is a group selected from

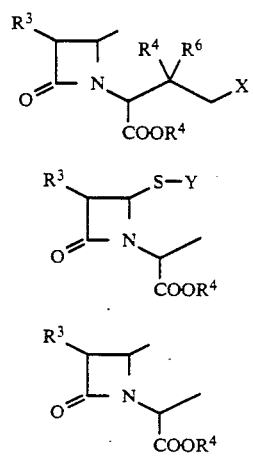

wherein $R^3$ is an amino group or a protected amino group, and $R^4$–$R^8$ are as defined in the application.

13 Claims, No Drawings

PROCESS FOR PREPARATION OF β-LACTAM DERIVATIVE FROM AN ALKENYL SUBSTITUTED β-LACTAM DERIVATIVE USING A RUTHENIUM OR RHENIUM CATALYST AND A PERIODIC ACID

BACKGROUND OF THE INVENTION

1. Field of the Invention

The present invention relates to a novel process for preparing a β-lactam derivative.

2. Prior Art

A process using ozone is widely known for preparing a β-lactam derivative represented by the following formula (2) and/or the corresponding enol tautomer (which may be produced depending on its structure) from an alkenyl-substituted β-lactam derivative represented by the following formula (1):

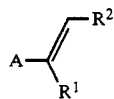
(1)

wherein $R^1$ is a hydrogen atom, a $C_{1-4}$ alkyl group or a $C_{1-4}$ haloakyl group, $R^2$ is a hydrogen atom, a $C_{1-4}$ alkyl group or a phenyl group which may have a substituent, A is a group represented by the formula

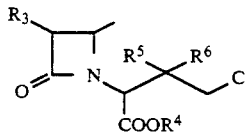

a group represented by the formula

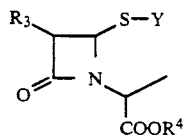

or a group represented by the formula

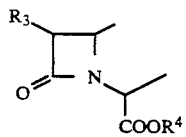

wherein $R^3$ is an amino group or a protected amino group, $R^4$ is a hydrogen atom or a group for protecting a carboxylic acid, one of $R^5$ and $R^6$ is a hydrogen atom and the other is either a hydroxyl group or a protected hydroxyl group, or $R^5$ and $R^6$, when taken together, represent an oxo group or a group represented by the formula

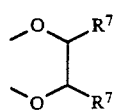

wherein $R^7$ is a hydrogen atom, a $C_{1-4}$ alkyl group, a phenyl group which may have a substituent, or a group —$COOR^8$ wherein $R^8$ is a hydrogen atom or a $C_{1-4}$ alkyl group, X is a hydrogen atom, a halogen atom, a hydroxyl group or a protected hydroxyl group, and Y is a group of the formula —$SO_2Ar$ or —$SAr$ wherein Ar is an aryl group which may have a substituent or a nitrogen-containing aromatic heterocyclic group which may have a substituent; and

(2)

wherein $R^1$ and A are as defined above (see, e.g. Japanese Unexamined Patent Publications Nos. 129590 1975 and No.98265/1976).

However, the process using ozone has the disadvantages of requiring special equipment and unavoidably producing a highly explosive ozonide as an intermediate during the ozone-oxidizing reaction, consequently involving a dangerous procedure. Another problem is that the ozone-oxidizing reaction must be conducted using ozone in the form of a dilute solution at an extremely low temperature, making it difficult to carry out the process on an industrial basis.

As described hereinbefore, the conventional processes for preparing the β-lactam derivative of the formula (2) from the alkenyl-substituted β-lactam derivative of the formula (1) by the oxidation of ozone are difficult to industrially practice and have various drawbacks to be overcome.

It is an object of the present invention to provide a novel process for preparing the derivative of the formula (2) and/or the corresponding enol tautomer with a high purity in a high yield from the derivative of the formula (1), the process being free of the drawbacks of the foregoing conventional processes, safe and convenient to perform and industrially fully feasible.

DETAILED DESCRIPTION OF THE INVENTION

We conducted extensive research to achieve the foregoing object and found that when a specific oxidizing agent is used, the reaction for oxidizing the derivative of the formula (1) is permitted to proceed smoothly and the foregoing object is completely fulfilled. The present invention has been accomplished based on this novel finding.

According to the present invention, there is provided a process for preparing a β-lactam derivative represented by the following formula (2) and/or the corresponding enol tautomer (which may be produced depending on its structure), the process comprising oxidizing an alkenyl-substituted β-lactam derivative represented by the following formula (1) in the presence of a ruthenium catalyst or a rhenium catalyst using a periodic acid:

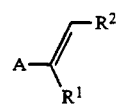
(1)

wherein $R^1$ is a hydrogen atom, a $C_{1-4}$ alkyl group or a $C_{1-4}$ haloakyl group, $R^2$ is a hydrogen atom, a $C_{1-4}$ alkyl group or a phenyl group which may have a substituent, A is a group represented by the formula a group represented by the formula

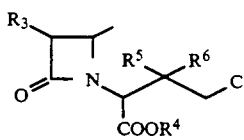

a group represented by the formula

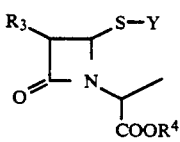

or a group represented by the formula

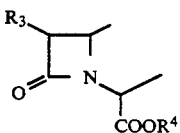

wherein $R^3$ is an amino group or a protected amino group, $R^4$ is a hydrogen atom or a group for protecting a carboxylic acid, one of $R^5$ and $R^6$ is a hydrogen atom and the other is either a hydroxyl group or a protected hydroxyl group, or $R^5$ and $R^6$, when taken together, represent an oxo group or a group represented by the formula

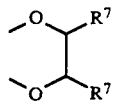

wherein $R^7$ is a hydrogen atom, a $C_{1-4}$ alkyl group, a phenyl group which may have a substituent, or a group $-COOR^8$ wherein $R^8$ is a hydrogen atom or a $C_{1-4}$ alkyl group, X is a hydrogen atom, a halogen atom, a hydroxyl group or a protected hydroxyl group, and Y is a group of the formula $-SO_2Ar$ or $-SAr$ wherein Ar is an aryl group which may have a substituent or a nitrogen-containing aromatic heterocyclic group which may have a substituent; and

 (2)

wherein $R^1$ and A are as defined above.

According to the invention, the derivative of the formula (2) and/or the corresponding enol tautomer can be safely and industrially prepared with a high purity in a high yield by means of simple procedure from the derivative of the formula (1) using a ruthenium catalyst or a rhenium catalyst and a periodic acid in combination.

Typical examples of the $C_{1-4}$ alkyl group are methyl, ethyl, n-propyl, isopropyl, n-butyl, isobutyl, tert-butyl, etc.

Specific examples of the $C_{1-4}$ haloalkyl group are methyl, ethyl, n-propyl, isopropyl, n-butyl, isobutyl, tert-butyl and the like which are replaced with 1 to 3 halogen atoms such as chlorine, bromine, iodine or the like.

Examples of the substituent which the phenyl group may have are fluorine atom, chlorine atom, bromine atom, iodine atom and like halogen atoms; methyl, ethyl, n-propyl, isopropyl, n-butyl, isobutyl, tert-butyl and like $C_{1-4}$ alkyl groups; methoxy, ethoxy, propoxy, isopropoxy, butoxy, isobutoxy, tert-butoxy and like $C_{1-4}$ alkoxy groups; nitro group; cyano group; amino, methylamino, dimethylamino, ethylamino, diethylamino and like amino groups which may have a $C_{1-4}$ alkyl group as a substituent; hydroxyl group; acetoxy group mercapto group; methylthio group; acetylthio group; acetyl group; etc. A suitable combination of 1 to 5 of these substituents which may be the same or different can be present as the substituent for the phenyl group.

Examples of the protected amino group include the groups described in Theodora W. Greene, "Protective Group in Organic Synthesis" (hereinafter simply referred to as "literature"), Chapter 7, pp 218–287, and phenoxyacetamide, p-methylphenoxyacetamide, p-methoxyphenoxyacetamide, p-chlorophenoxyacetamide, p-bromophenoxyacetamide, phenylacetamide, p-methylphenylacetamide, p-methoxyphenylacetamide, p-chlorophenylacetamide, p-bromophenylacetamide, phenylmonochloroacetamide, phenyldichloroacetamide, phenylhydroxyacetamide, phenylacetoxyacetamide, α-oxophenylacetamide, thienylacetamide, benzamide, p-methylbenzamide, p-methoxybenzamide, p-chlorobenzamide, p-bromobenzamide, phenylglycylamide, phenylglycylamide with the amino group fully protected, p-hydroxyphenylglycylamide, p-hydroxyphenylglycylamide with one or both of amino group and hydroxyl group fully protected, etc. Examples of protective groups for the amino group of phenylglycylamide and p-hydroxyphenylglycylamide include the groups stated in the foregoing literature, Chapter 7, pp 218–287. Examples of protective groups for the hydroxyl group of p-hydroxyphenylglycylamide include those described in the foregoing literature, Chapter 2, pp 10–72.

Examples of protective groups for the carboxylic acid include the groups exemplified in said literature, Chaper 5, pp 152–192, and benzyl group, p-methoxybenzyl group, p-nitrobenzyl group, diphenylmethyl group, trichloroethyl group, tert-butyl group, etc.

Examples of protective groups for the protected hydroxyl group are the groups set forth in said literature, Chaper 2, pp 10–72, and methyl group, ethyl group, isopropyl group, tert-butyl group, benzyl group, p-methylbenzyl group, p-methoxybenzyl group, diphenylmethyl group, trimethylsilyl group, tert-butyldimethylsilyl group, triethylsilyl group, phenyldimethylsilyl group, acetyl group, etc.

Halogen atoms include fluorine atom, chlorine atom, bromine atom, iodine atom, etc.

Typical examples of the aryl group Ar which may have a substituent are unsubstituted aryl groups such as phenyl group, naphthyl group and the like, substituted aryl groups having one of the substituents exemplified below, or two or more thereof which are different or the same (e.g. 5 or less phenyl groups, or 7 or less naphthyl groups). Specific examples of the above substituents include fluorine atom, chlorine atom, bromine atom, iodine atom and like halogen atoms; methyl, ethyl, n-propyl, isopropyl, n-butyl, isobutyl, tert-butyl and like $C_{1-4}$ alkyl groups; methoxy, ethoxy, propoxy, isopropoxy, butoxy, isobutoxy, tert-butoxy and like $C_{1-4}$ alkoxy groups; methylthio, ethylthio, n-propylthio, isopropylthio, n-butylthio, isobutylthio, tert-butylthio and like $C_{1-4}$ alkylthio groups; amino, methylamino, dimethylamino, ethylamino, diethylamino and like amino groups which may have 1 to 2 $C_{1-4}$ alkyl groups as the substituent; hydroxyl group; nitro group; cyano group; phenyl group; acyloxy group represented by the formula —OCOR$^9$ wherein R$^9$ is phenyl group, tolyl group or $C_{1-4}$ alkyl group; acyl group represented by the formula —COR$^9$ wherein R$^9$ is as defined above); etc.

Specific examples of the nitrogen-containing aromatic heterocyclic group Ar which may have a substituent are unsubstituted nitrogen-containing aromatic heterocyclic groups of the following formulas

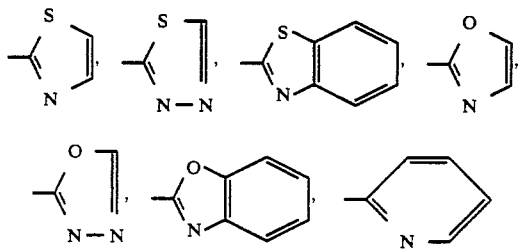

and substituted nitrogen-containing aromatic heterocyclic groups having one or more of substituents which are the same as those in said substituted aryl groups.

It is essential in the invention to oxidize the alkenyl-substituted β-lactam derivative of the formula (1) with a periodic acid in the presence of a ruthenium catalyst or a rhenium catalyst.

The ruthenium catalyst for use in the invention can be any of conventional ruthenium compounds in the form of an oxide, halide, complex salt and the like. Examples of useful ruthenium compounds are $Ru(CO)_5$, $Ru(CO)_9$, $Ru_3(CO)_{12}$, $Ru(NO)_5$, $Ru(CO)_4$, $Ru(CO)Br$, $Ru(CO_2)Cl_2$, $Ru(CO_2)Br_2$, $Ru(CO)_2I_2$, $Ru(NO)Br_2$, $Ru(NO)I_2$, $H_4[Ru(CN)_6]$, $Na_4[Ru(CN)_6]$, $K_4[Ru(CN)_6]$, $Ca_2[Ru(CN)_6]$, $Sr_2[Ru(CN)_6]$, $Ba_2[Ru(CN)_6]$, $[Ru(phen)_3]Cl_2$, $[Ru(phen)_3]I_2$, $[Ru(phen)_3](ClO_4)_2$, $RuS_2$, $RuSe_2$, $RuTe_2$, $RuCl_3$, $RuBr_3$, $RuI_3$, $Na_3[RuCl_6]$, $K_3[RuCl_6]$, $Na_2[RuCl_5(OH)_2]$, $K_2[RuCl_5(OH)_2]$, $Na_2[RuCl_5(NO)]$, $K_2[RuCl_5(NO)]$, $[Ru(NH_3)_6]Cl_3$, $[Ru(NH_3)_6]Br_3$, $[Ru(NH_3)_6]I_3$, $Ru(acac)_3$, $RuO_2$, $Na_2[RuCl_6]$, $K_2[RuCl_6]$, $Na_4[Cl_5RuORuCl_5]$, $RuF_5$, $H_2RuO_4$, $(NH_4)_2RuO_4$, $Na_2RuO_4$, $K_2RuO_4$, $NaRuO_4$, $KRuO_4$, $RuO_4$, etc. These ruthenium compounds can be also advantageously used in the form of a hydrate in the invention. Among the above ruthenium compounds, $RuCl_3$, $RuBr_3$, $RuI_3$ and $RuO_2$ are preferred.

The rhenium catalyst for use in the invention can be any of conventional rhenium compounds in the form of an oxide, sulfide, halide, complex salt, etc. Typical examples include $Re_2O_3$, $ReCl_3$, $ReBr_3$, $Na[ReCl_4]$, $K[ReCl_4]$, $ReO_2$, $Na_2ReO_3$, $K_2ReO_3$, $ReS_2$, $ReF_4$, $K_2[ReCl_6]$, $Cs_2[ReCl_6]$, $(NH_4)_2[ReCl_6]$, $NaReO_3$, $KReO_3$, $K_2[ReOCl_5]$, $(NH_4)_2[ReOCl_5]$, $ReCl_5$, $ReO_3$, $Na_2ReO_4$, $K_2ReO_4$, $ReF_6$, $ReOF_4$, $ReO_2F_2$, $ReOCl_4$, $Re_2O_7$, $NaR_4O_4$, $KReO_4$, $Re_2S_7$, $NaReO_3S$, $KReO_3S$, $ReO_3Cl$, $ReO_3Br$, etc. These rhenium compounds may be used also in the form of a hydrate in the invention. Among the above examples, a preferred rhenium compound is $Re_2O_7$.

The amount of ruthenium or rhenium catalyst used theoretically suffices if it results in the presence of one molecule in the reaction system. A typical amount is in the range of about 0.0001 to about 0.5 mole, preferably about 0.001 to about 0.2 mole, per mole of the compound of the formula (1).

Examples of useful periodic acids are orthoperiodic acid, metaperiodic acid, among which a metaperiodic acid is preferred.

The amount of the periodic acid to be used is variable depending on the kind of the compound to be reacted, typically in the range of about 1 to 15 moles, preferably about 1 to 8 moles, per mole of the compound of the formula (1) when the compound of the formula (1) has one alkenyl group as the substituent. Yet the amount is double if the compound of the formula (1) has two alkenyl groups as the substituents.

The oxidizing reaction of the invention is carried out in an organic solvent or a water-containing organic solvent or in a two-phase system if the organic solvent used is immiscible with water. Useful organic solvents include a wide range of conventional ones which are capable of dissolving the compound of the formula (1) and which remain inactive under the reaction conditions. Examples of useful organic solvents are methanol, ethanol, propanol, isopropanol, butanol, tert-butanol and like alcohols, methyl formate, ethyl formate, propyl formate, butyl formate, methyl acetate, ethyl acetate, propyl acetate, butyl acetate, methyl propionate, ethyl propionate and like lower alkyl esters of lower carboxylic acids, acetone, methyl ethyl ketone, methyl propyl ketone, methyl butyl ketone, methyl isobutyl ketone, diethyl ketone and like ketones, diethyl ether, ethyl propyl ether, ethyl butyl ether, dipropyl ether, diisopropyl ether, dibutyl ether, methyl cellosolve, dimethoxyethane and like ethers, tetrahydrofuran, dioxane and like cyclic ethers, acetonitrile, propionitrile, butyronitrile, isobutyronitrile, valeronitrile and like nitriles, benzene, toluene, xylene, chlorobenzene, anisole and like substituted or unsubstituted aromatic hydrocarbons, dichloromethane, chloroform, dichloroethane, trichloroethane, dibromoethane, propylenedichloride, carbon tetrachloride, freons and like halogenated hydrocarbon, pentane, hexane, heptane, octane and like aliphatic hydrocarbons, cyclopentane, cyclohexane, cycloheptane, cyclooctane and like cycloalkanes, dimethylformamide, dimethylacetamide and like amides, dimethylsulfoxides, etc. These organic solvents can be used singly or at least two of them are usable in mixture. The organic solvent may contain water, when so required. The amount of the organic solvent used is about 0.5 to about 200 l, preferably about 1 to about 50 l, per kilogram of the compound of the formula (1).

A suitable oxidizing reaction temperature employable in the invention is variable depending on the kinds of the starting compound, catalyst, solvent and like substances used, typically in the range of about −20° to about 50° C., preferably about −5° to about 30° C.

After completion of the reaction, the contemplated β-lactam derivative of the formula (2) and/or the corresponding enol tautomer producible depending its structure can be obtained by separation from the reaction product, for example, by means of conventional extraction techniques. The obtained desired compound can be purified, when required, by common purification procedures such as recrystallization, column chromatography, etc.

According to the present invention, the β-lactam derivative of the formula (2) and/or the corresponding enol tautomer producible depending on its structure can be easily and safely produced with a high purity in a high yield by means of simple procedure without use of specific apparatus, using easily available equipment and medicinal agent, etc.

EXAMPLES

The present invention will be described below in greater detail with reference to the following examples.

EXAMPLE 1

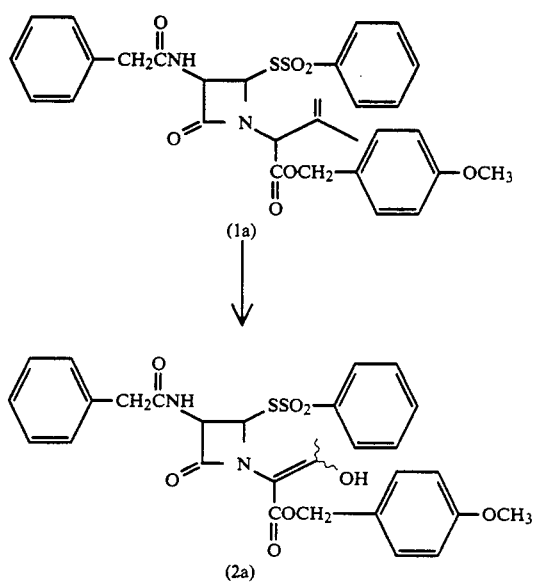

The above compound (1a) was dissolved in a solvent mixture of 20 ml of acetone and 10 ml of water, and the resulting solution was cooled in an ice bath. To the solution were added 2 g of periodic acid and 2.2 mg of ruthenium dioxide, and the resulting mixture was reacted with stirring for 4 hours. A 50 ml quantity of water was added to the reaction mixture obtained above and the mixture was extracted with 50 ml of ethyl acetate. The organic layer was separated, washed with a mixture of 10 ml of a 5% aqueous solution of hypo, 10 ml of a 5% aqueous solution of sodium hydrogen carbonate and 20 ml of a saturated saline solution and dried over anhydrous magnesium sulfate. The residue thus obtained was concentrated under reduced pressure, giving the desired compound (2a) in a yield of 98%.

The NMR spectrum data on this compound were identical with those on an authentic compound (2a) synthesized by another process.

EXAMPLE 2

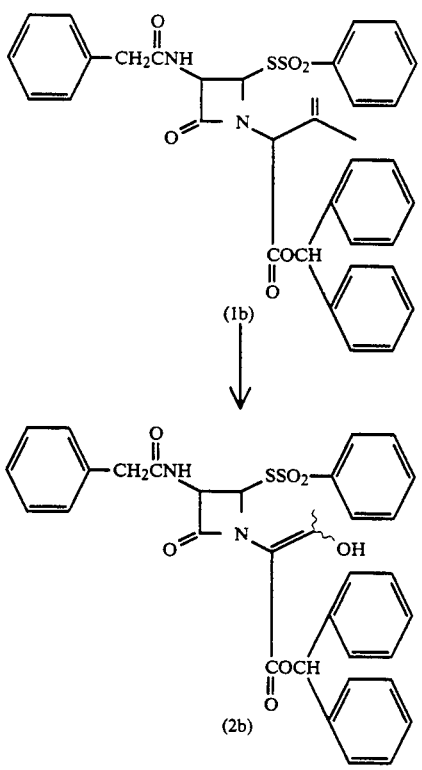

The above compound (1b) was reacted in the same manner as in Example 1, giving the desired compound (2b) in a yield of 96%.

The NMR spectrum data on this compound were identical with those on an authentic compound (2b) synthesized by another process.

EXAMPLE 3

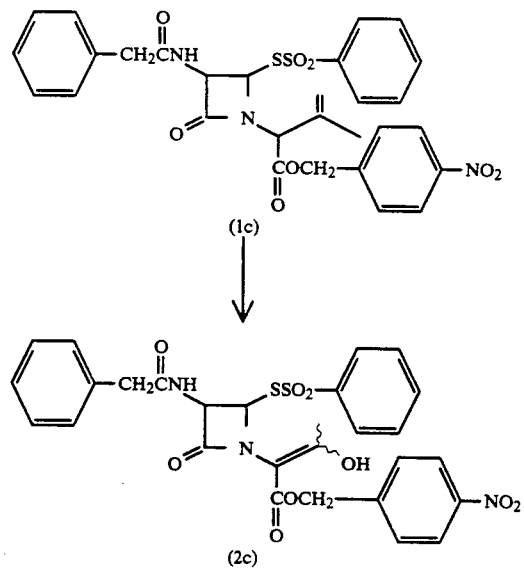

The desired compound (2c) was prepared in a yield of 95% by reacting the above compound (1c) in the same manner as in Example 1.

The NMR spectrum data on this compound were obtained were identical with those on an authentic compound (2c) synthesized by another process.

EXAMPLE 4

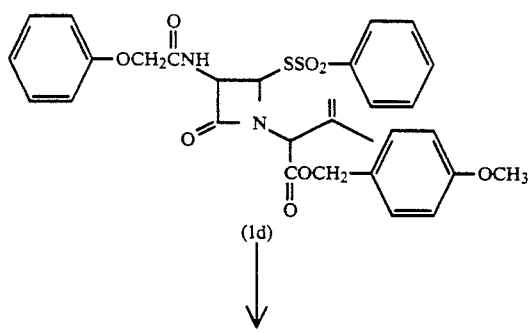

(1d)

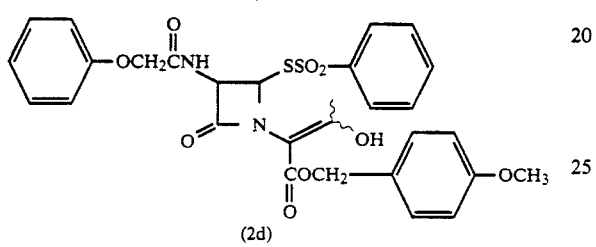

(2d)

The desired compound (2d) was produced in a yield of 90% by reacting the above compound (1d) in the same manner as in Example 1.

The NMR spectrum data on the thus obtained compound (2d) were identical with those on an authentic compound (2c) synthesized by another process.

EXAMPLE 5

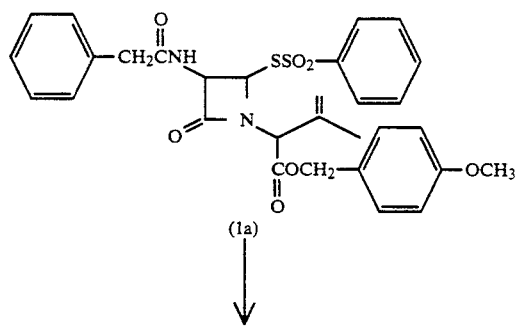

(1a)

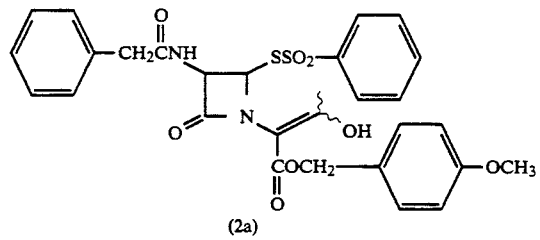

(2a)

The above compound (1a) and 200 mg of periodic acid were dissolved in a solvent mixture of 2 ml of tetrahydrofuran and 1 ml of water. A 5 mg quantity of Re₂O₇ was added to the solution obtained above and the mixture was reacted with stirring at room temperature for 21 hours.

A 10 ml quantity of water was added to the reaction mixture obtained above and the resulting mixture was extracted with 10 ml of ethyl acetate. The organic layer was separated, washed with a mixture of 1 ml of a 5% aqueous solution of hypo, 1 ml of a 5% aqueous solution of sodium hydrogen carbonate and 5 ml of a saturated saline solution and dried over anhydrous magnesium sulfate. The resulting residue was concentrated under reduced pressure, giving the desired compound (2a) in a yield of 85%.

The NMR spectrum data on the thus obtained compound were identical with those obtained with an authentic compound (2a) prepared by another process.

EXAMPLE 6

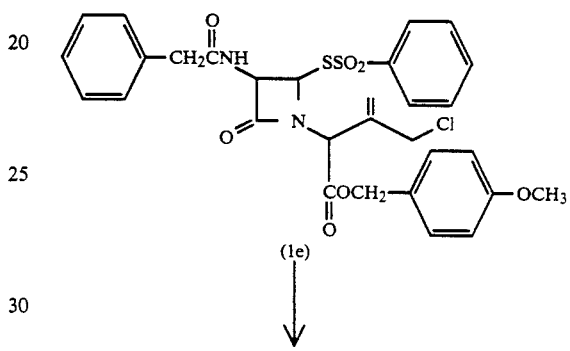

(1e)

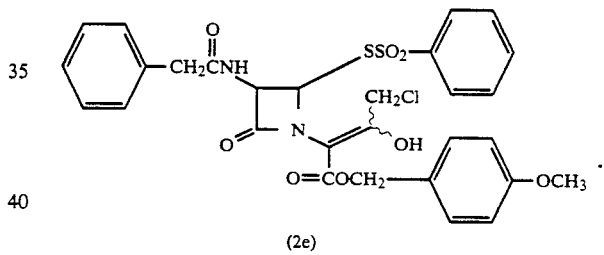

(2e)

A 100 mg quantity of the above compound (1e) was dissolved in a solvent mixture of 2 ml of acetone and 1 ml of water. The obtained solution was cooled to 15° C., 200 mg of periodic acid and 1 mg of ruthenium dioxide were added thereto and the resulting mixture was reacted with stirring for 40 minutes.

A 10 ml quantity of water wa added to the reaction mixture obtained above and the resulting mixture was extracted with 10 ml of ethyl acetate. The organic layer was separated, washed with a mixture of 1 ml of a 5% aqueous solution of hypo, 1 ml of a 5% aqueous solution of sodium hydrogen carbonate and 5 ml of a saturated saline solution and dried over anhydrous magnesium sulfate. The residue obtained was concentrated under reduced pressure, giving the desired compound (2e) in a yield of 92%.

NMR spectrum (CDCl₃) δ (ppm): 3.60 (s, 2H), 3.80 (s, 3H), 4.23 (ABq, 2H, J=13.0 Hz), 4.73 (dd, 1H, J=5.0 Hz, 7.0 Hz) 5.12 (ABq, 2H, J=13.0 Hz) 5.71 (d, 1H, J=5.0 Hz), 6.27 (d, 1H, J=7.0 Hz) 6.80–8.00 (m, 14H).

EXAMPLE 7

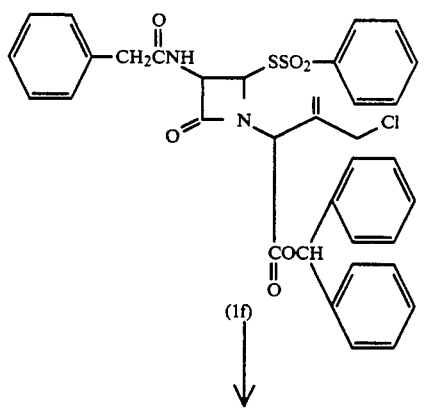

(1f)

↓

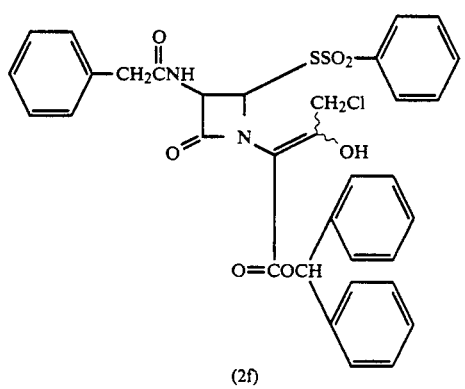

(2f)

The above compound (1f) was reacted in the same manner as in Example 6, giving the desired compound (2f) in a yield of 92%.

NMR spectrum (CDCl₃) δ (ppm): 3.63 (s, 2H), 4.20 (ABq, 2H, J=13.0 Hz) 4.76 (dd, 1H, J=5.0 Hz, 7.0 Hz) 5.72 (d, 1H, J=5.0 Hz), 6.10 (d, 1H, J=7.0 Hz) 6.85 (s, 1H), 7.05-7.50 (m, 20H).

EXAMPLE 8

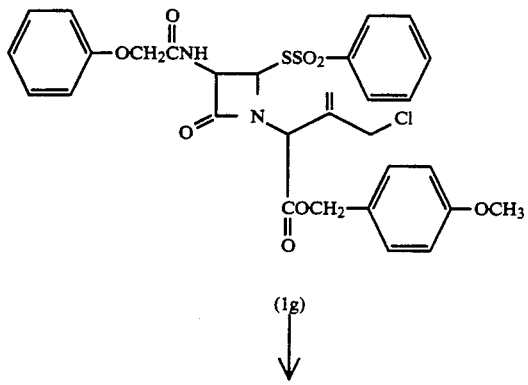

(1g)

↓

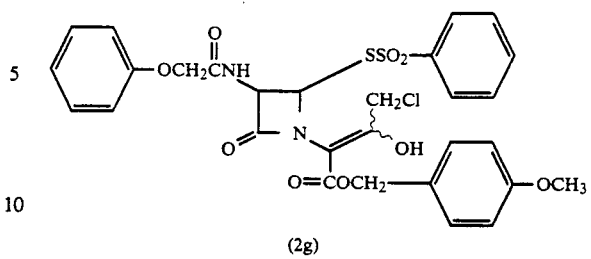

(2g)

The above compound (1g) was reacted in the same manner as in Example 6, giving the desired compound (2g) in a yield of 90%.

NMR spectrum (CDCl₃) δ (ppm): 3.70 (s, 2H), 3.80 (s, 3H) 4.23 (ABq, 2H, J=13.0 Hz) 4.94 (dd, 1H, J=6.0 Hz, 8.0 Hz) 5.15 (ABq, 2H, J=13.0 Hz), 5.78 (d, 1H, J=6.0 Hz) 6.75-7.95 (m, 14H).

EXAMPLE 9

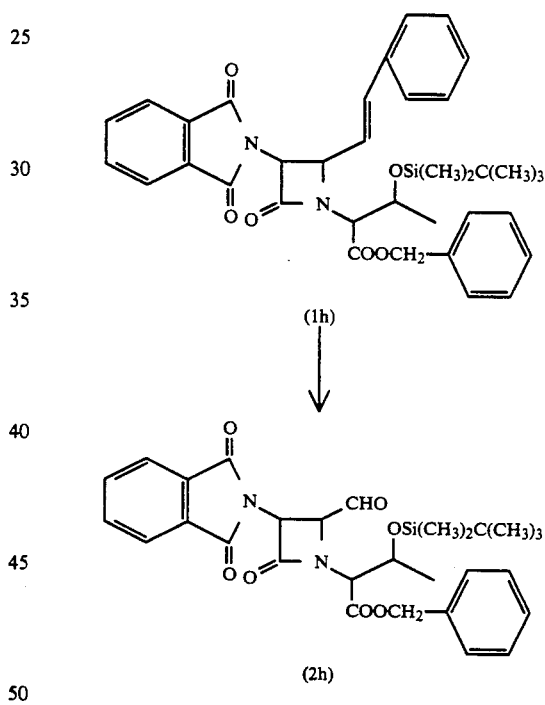

(1h)

↓

(2h)

A 500 mg quantity of the above compound (1h) was dissolved in 10 ml of acetone and 2.5 ml of water was added thereto. The resulting mixture was cooled in an ice bath, 875 mg of periodic acid and 5 mg of RuCl₃ were added and the resulting mixture was reacted with stirring at 3° C. for 4 hours.

To the reaction mixture thus obtained were added an aqueous solution of hypo and an aqueous solution of sodium hydrogen carbonate. The resulting mixture was extracted with benzene and the organic layer was separated. The organic layer was dried over anhydrous magnesium sulfate and concentrated under reduced pressure, giving the desired compound (2h) in a yield of 86%.

NMR spectrum (CDCl₃) δ (ppm):
0.05 (s, 3H), 0.10 (s, 3H) 0.75 (s, 9H), 1.55 (d, 3H, J=12.0 Hz) 4.60 (m, 2H) 4.80 (dd, 1H, J=6.0 Hz, 9.0

Hz) 5.13 (ABq, 2H, J=12.0 Hz), 5.65 (d, 1H, J=9.0 Hz) 7.15-7.85 (m, 9H) 9.85 (d, 1H, J=6.0 Hz).

EXAMPLE 10

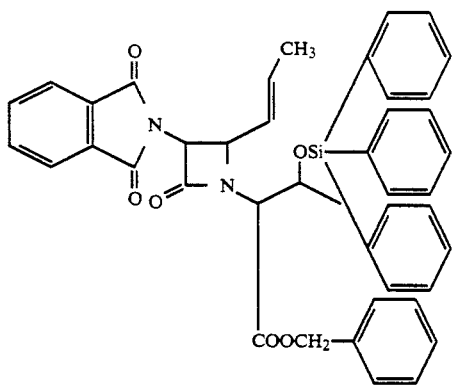

(1i)

↓

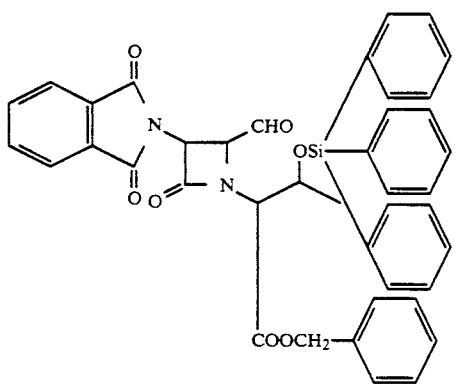

(2i)

The above compound (1i) was reacted in the same manner as in Example 9, giving the desired compound (2i) in a yield of 85%.

NMR spectrum (CDCl₃) δ (ppm): 1.53 (d, 1H, J=8.5 Hz) 4.30-4.80 (m, 2H) 5.05 (dd, 1H, J=6.0 Hz, 8.5 Hz) 4.98 (ABq, 2H, J=22 Hz), 5.77 (d, 1H, J=8.5 Hz) 6.90-7.90 (m, 24H) 10.00 (d, 1H).

EXAMPLE 11

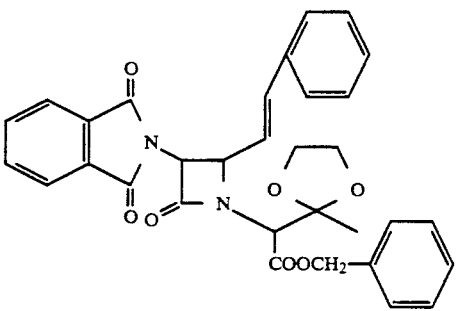

(1j)

↓

-continued

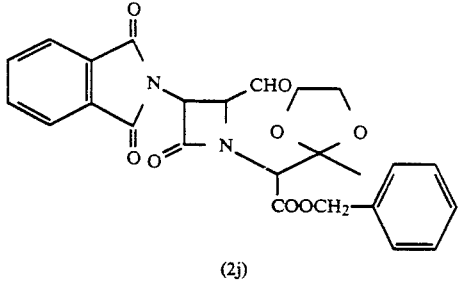

(2j)

The above compound (1j) (a mixture of diastereomers in the bonded carbon atom of the ester group) was reacted in the same manner as in Example 9, giving the desired compound (2j) (diastereomer mixture) in a yield of 94%.

NMR spectrum (CDCl₃) δ (ppm): 1.65, 1.39 (ss, 3H) 3.50-3.95 (m, 4H) 4.60-4.80 (m, 1H) 5.18, 5.23 (ABq, ABq, 1H, J=24 Hz) 5.10-5.25 (m, 1H), 5.55, 5.62 (d, d, 1H, J=6.0 Hz) 6.65-7.90 (m, 9H) 9.73, 9.81 (d, d, 1H, J=6.0 Hz).

We claim:

1. A process for preparing a β-lactam derivative conforming to formula (2):

wherein:
R¹ is a hydrogen atom, a $C_{1-4}$ alkyl, or a $C_{1-4}$ haloalkyl group;
A is a radical selected from the group consisting of

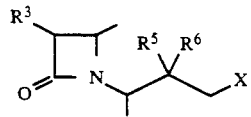

and

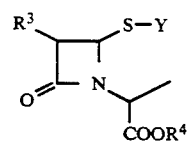

wherein
wherein $R^3$ is an amino group or a protected amino group;
$R^4$ is a hydrogen atom or a protecting group for a carboxylic acid;
$R^5$ is a hydrogen atom, a hydroxyl group, or a protected hydroxyl group;
$R^6$ is a hydrogen atom, a hydroxyl group, or a protected hydroxyl group, with the proviso that one of $R^5$ and $R^6$ is a hydrogen atom and the other is either a hydroxyl group or a protected hydroxyl group, or $R^5$ and $R^6$ taken together represent an oxo group or a group represented by the formula

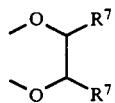

wherein $R^7$ is a hydrogen atom, a $C_{1-4}$ alkyl group, an optionally substituted phenyl group, or a —$COOR^8$;

$R^8$ is a hydrogen atom or a $C_{1-4}$ alkyl group;

X is a hydrogen atom, a halogen atom, a hydroxyl group, or a protected hydroxyl group;

Y is —$SO_2Ar$ or —SAr;

Ar is an optionally substituted aryl group or an optionally substituted nitrogen-containing aromatic heterocyclic group, said process comprising oxidizing an alkenyl-substituted β-lactam derivative with periodic acid in the presence of a catalyst selected from the group consisting of ruthenium and rhenium catalysts, with the proviso that said alkenyl-substituted β-lactam derivative conforms to formula (1):

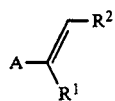

wherein A and $R^1$ are as defined above; and $R^2$ is a hydrogen atom, a $C_{1-4}$ alkyl, or an optionally-substituted phenyl group.

2. A process according to claim 1 wherein the ruthenium catalyst is an oxide, a halide or a complex salt of ruthenium or a hydrate thereof.

3. A process according to claim 1 wherein the rhenium catalyst is an oxide, a halide or a complex salt of rhenium or a hydrate thereof.

4. A process according to claim 1 wherein the amount of the catalyst used is about 0.0001 to about 0.5 mole per mole of the alkenyl-substituted β-lactam derivative.

5. A process according to claim 4 wherein the amount of the catalyst used is about 0.001 to about 0.2 mole per mole of the alkenyl-substituted β-lactam derivative.

6. A process according to claim 1 wherein the periodic acid is an orthoperiodic acid or a metaperiodic acid.

7. A process according to claim 6 wherein the periodic acid is a metaperiodic acid.

8. A process according to claim 1 wherein the amount of the periodic acid used is about 1 to about 15 moles per mole of the alkenyl-substituted β-lactam derivative which has one alkenyl group as the substituent.

9. A process according to claim 8 wherein the amount of the periodic acid used is about 1 to about 8 moles per mole of the alkenyl-substituted β-lactam derivative which has one alkenyl group as the substituent.

10. A process according to claim 8 wherein the amount of the periodic acid used when the alkenyl-substituted β-lactam derivative has two alkenyl groups as substituents is double the amount thereof when the alkenyl-substituted β-lactam derivative has one alkenyl group as the substituent.

11. A process according to claim 1 wherein the reaction is conducted in an organic solvent, a water-containing organic solvent or a two-phase system consisting of water and an organic solvent which is immiscible with water.

12. The process of claim 1, wherein said nitrogen-containing heterocyclic group has a condensed benzene ring.

13. The process of claim 1, wherein said nitrogen-containing heterocyclic group contains one oxygen or sulfur atom.

* * * * *